United States Patent
Bjork

(10) Patent No.: US 10,874,524 B2
(45) Date of Patent: Dec. 29, 2020

(54) EXPANDABLE INTERBODY DEVICE

(71) Applicant: Spineology Inc., St. Paul, MN (US)

(72) Inventor: Todd M. Bjork, Hudson, WI (US)

(73) Assignee: Spineology Inc., St. Paul, MN (US)

( * ) Notice: Subject to any disclaimer, the term of this patent is extended or adjusted under 35 U.S.C. 154(b) by 702 days.

(21) Appl. No.: 15/393,216

(22) Filed: Dec. 28, 2016

(65) Prior Publication Data

US 2017/0181863 A1 Jun. 29, 2017

Related U.S. Application Data

(60) Provisional application No. 62/271,878, filed on Dec. 28, 2015.

(51) Int. Cl.
| | | |
|---|---|---|
| *A61F 2/44* | (2006.01) | |
| *A61F 2/46* | (2006.01) | |
| *A61F 2/30* | (2006.01) | |

(52) U.S. Cl.
CPC ............. *A61F 2/447* (2013.01); *A61F 2/442* (2013.01); *A61F 2/4611* (2013.01); *A61F 2002/3023* (2013.01); *A61F 2002/3054* (2013.01); *A61F 2002/30065* (2013.01); *A61F 2002/30322* (2013.01); *A61F 2002/30471* (2013.01); *A61F 2002/30518* (2013.01); *A61F 2002/30579* (2013.01); *A61F 2002/30581* (2013.01); *A61F 2002/30622* (2013.01)

(58) Field of Classification Search
CPC ...... A61F 2/442; A61F 2/4425; A61F 2/4455; A61F 2/446; A61F 2002/443
See application file for complete search history.

(56) References Cited

U.S. PATENT DOCUMENTS

| | | | | |
|---|---|---|---|---|
| 6,974,480 B2 * | 12/2005 | Messerli | ................. | A61F 2/446 623/17.16 |
| 7,431,735 B2 * | 10/2008 | Liu | ........................ | A61F 2/446 623/17.11 |
| 8,512,409 B1 * | 8/2013 | Mertens | ................... | A61F 2/447 623/17.11 |
| 2002/0161444 A1 * | 10/2002 | Choi | ........................ | A61F 2/446 623/17.11 |
| 2007/0021835 A1 * | 1/2007 | Edidin | ..................... | A61F 2/441 623/17.12 |
| 2009/0306777 A1 * | 12/2009 | Widmer | ............. | A61B 17/0401 623/13.14 |

\* cited by examiner

*Primary Examiner* — Anu Ramana
(74) *Attorney, Agent, or Firm* — Skaar Ulbrich Macari, P.A.

(57) ABSTRACT

An expandable interbody device for use in the spine is configured to fit through Kambin's Triangle. The expandable interbody device can include a body defining a front end, a rear end and a plurality of sidewalls spanning between the front and rear ends, an expandable member pivotally attached to the body such that the expandable member pivots outwardly from one of the plurality of sidewalls and a screw threaded into the body through the rear end thereof. The expandable member defines an actuator flange that projects into the body. The screw abuts the actuator flange such that contracting the screw into the body causes the expandable member to pivot outwardly from the body.

18 Claims, 8 Drawing Sheets

EXPANDABLE INTERBODY DEVICE

PRIORITY

This application claims the benefit of U.S. Provisional Application Ser. No. 62/271,878, filed on Dec. 28, 2015, which is hereby incorporated herein by reference in its entirety.

FIELD

The present invention generally relates to an expandable interbody device or a spacer for use in the spine. More particularly, the present invention relates to an expandable interbody device configured to fit through Kambin's Triangle and expand upon insertion.

BACKGROUND

It is desirable to spare the facet joint when placing spacers for intervertebral stabilization, support and fusion. There is a need for a spacer that is small enough to fit through Kambin's Triangle, yet able to expand upon insertion to fully support and/or stabilize the intervertebral space.

SUMMARY

The disclosure includes an expandable interbody device or spacer may be placed via a facet sparing, transforaminal approach. In an embodiment, the expandable interbody device of the present invention may be placed through a minimally invasive operative access. In another embodiment, the expandable interbody device of the present invention may be placed through a percutaneous operative access. The expandable interbody device may be partially or entirely formed of PEEK material.

The disclosure includes an expandable interbody device comprising a body defining a front end, a rear end and a plurality of sidewalls spanning between the front and rear ends, an expandable member pivotally attached to the body such that the expandable member pivots outwardly from one of the plurality of sidewalls and a screw threaded into the body through the rear end thereof. The expandable member defines an actuator flange that projects into the body. The screw abuts the actuator flange such that contracting the screw into the body causes the expandable member to pivot outwardly from the body.

The device of the present invention may be inserted into an intervertebral disc space while sparing the facet joint. For example, the device can be sized to fit through Kambin's triangle via a far lateral surgical approach, thus sparing the facet joint.

According to one example embodiment, the expandable interbody device may be sized to be placed through a 15 mm×6 mm area at the L4-L5 vertebra. However, the expandable interbody device may be placed at any other desired vertebral level.

The expandable interbody device may contain bone graft. According to one aspect, the expandable interbody device of the present invention may include an opening for bone graft insertion.

The expandable interbody device may be configured to allow bony ingrowth through the spacer.

The expandable interbody device may include an anti-backout feature.

The disclosure includes an expandable interbody device that is configured to rotate at least a portion thereof from a first insertion position to a second implanted position. In one example, the expandable interbody device may be inserted in a first collapsed geometry and expanded to a second geometry after placement. The expandable interbody device may include arms, wings or other expandable members. The expandable members may be solid such that fill material cannot escape back out of the entrance hole. The expandable members may alternatively include slots or slits to allow bone ingrowth.

The expandable interbody device may include a PEEK film configured to maintain the spacer in a collapsed geometry. The device can be partially or completely disposed within the PEEK film. An expansion tool may be configured to pierce the PEEK film allowing the arms, wings or other expandable members to expand.

The expandable interbody device may be expanded using a screw or other suitable mechanism. The expandable interbody device may employ a ramp mechanism for expansion.

The expandable interbody device may include a central strut having a diversion configured to split a stream of bone or other fill material directing the fill material to both sides of the strut.

The arms, wings or other expandable members may be pivotally or otherwise movably attached to the spacer body.

The expandable interbody device may include an asymmetrical taper along the implant width.

The expandable interbody device of the present invention may include lateral support features to help the implant stay upright when the disc space is subjected to shear forces.

A mesh container may be used in conjunction with the expandable interbody device to contain fill material. The mesh container can be configured as an expandable container and may be secured to the device.

The disclosure additionally includes a method of implanting an intervertebral device in a patient's spine. The method can include passing an implantable device in a contracted state through Kambin's Triangle to deliver the implantable device to an intervertebral location of the patient's spine, turning a screw disposed in the implantable device to deploy an expandable member, and introducing fill material through a channel formed through the screw to fill a cavity defined in the intervertebral location by a body of the implantable device and the expandable member.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
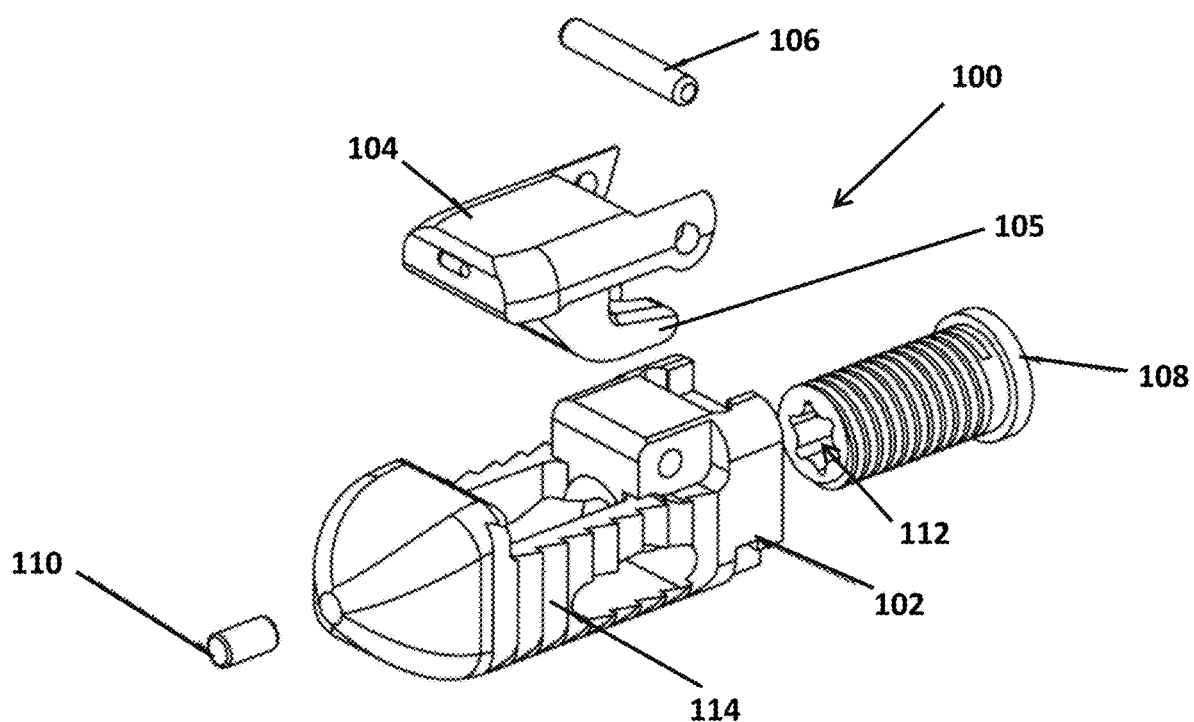
FIG. 1 depicts a perspective exploded view of an embodiment of the present invention.
Figure 2:
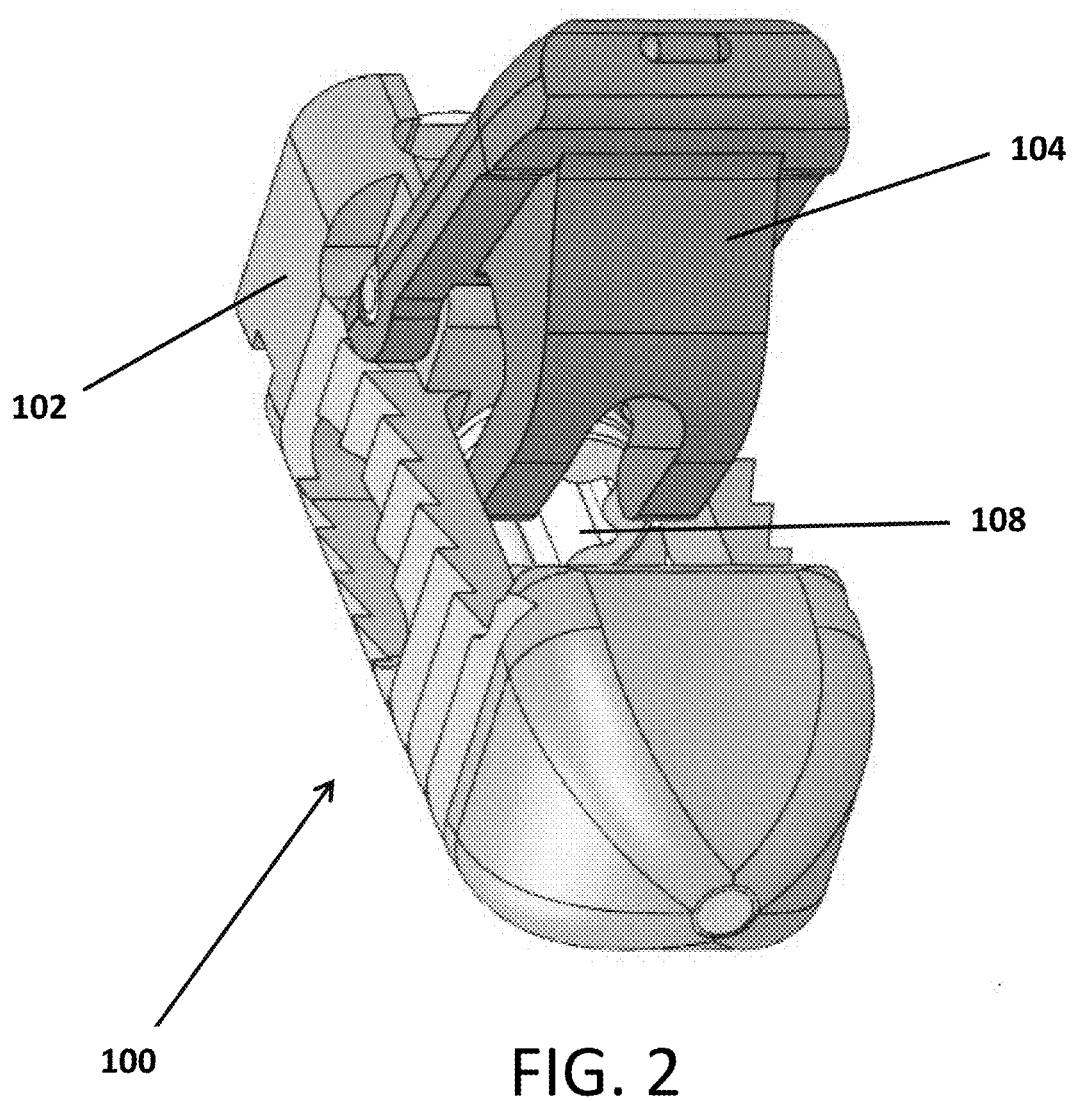
FIG. 2 depicts a perspective view of an embodiment of the present invention.
Figure 3:
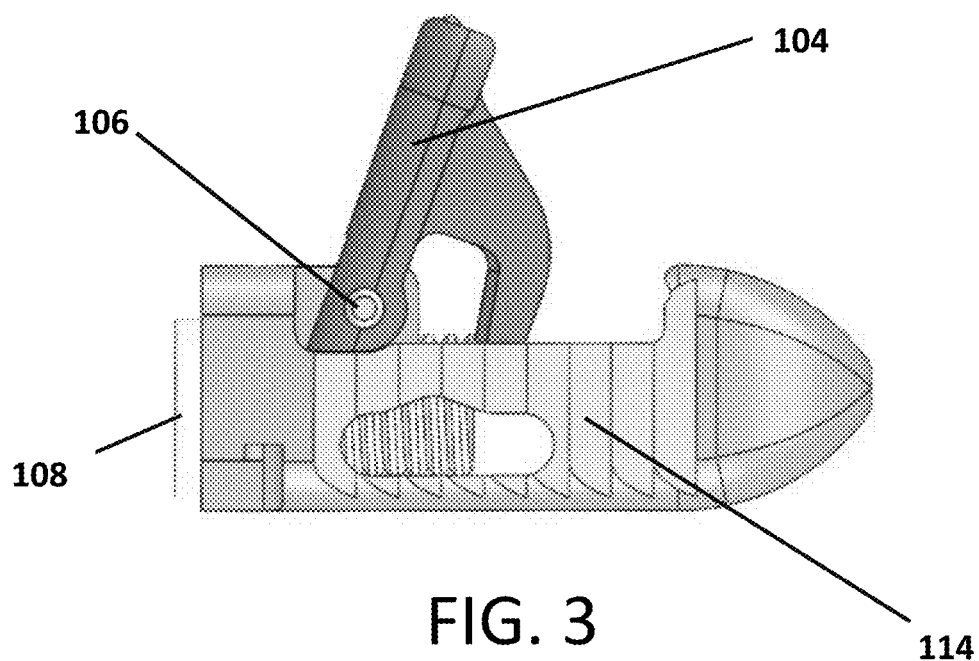
FIG. 3 depicts a side view of an embodiment of the present invention.
Figure 4:
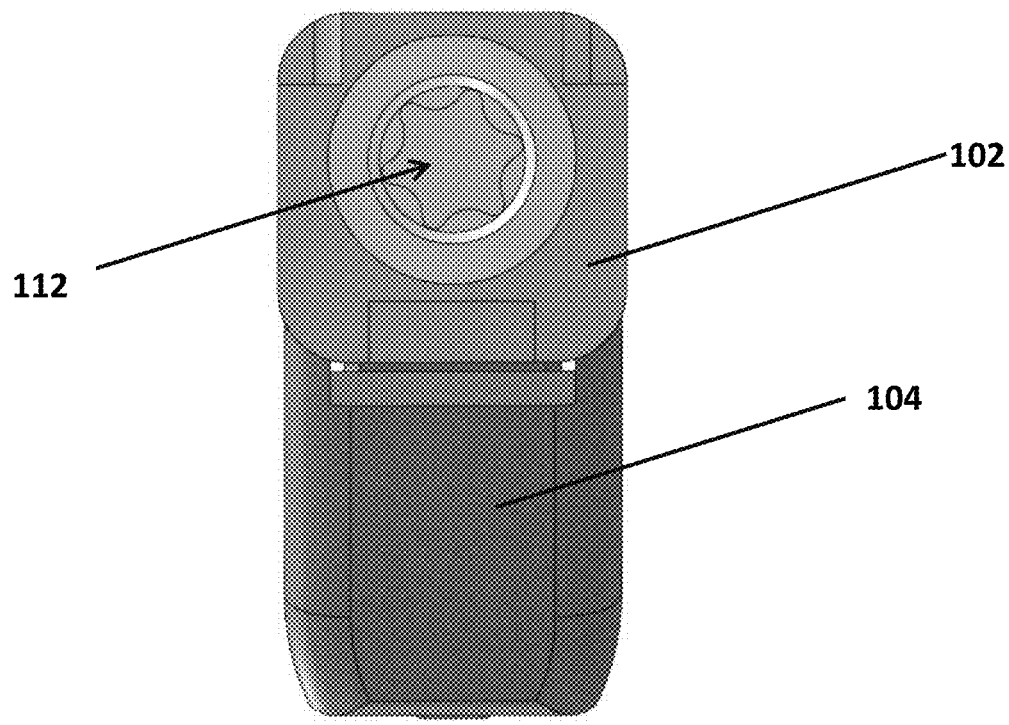
FIG. 4 depicts an end view of an embodiment of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Referring to FIGS. 1-10, an expandable interbody device 100 is shown. The device includes a main body 102 and a pivotal wing or arm 104 attached to the body 102 by a hinge pin 106. A screw 108 is threaded into the body 102 such that it contacts an actuator flange 105 of the arm 104 to cause the arm 204 to pivot outward from the body 102 as the screw is contracted into the body as it rotates.

A marker pin 110 can be inserted into the head or front portion of the body 102. The marker pin 110 can be a material (e.g., Tantalum) that is visible under indirect observation such as x-ray or fluoroscopy. This enables the surgeon to more easily view the implant position and orientation with respect to the patient's tissues during the surgical procedure since the body 102 may be formed of a material that is not easily viewed via indirect observation.

In use, the expandable interbody device 100 can be inserted in the compacted or shut configuration though a very narrow opening in the patient's anatomy, such as through an area of no more than 15 mm×6 mm. The device 100 can then be rotated into a position allowing for easier access while passing by the patient's nerve roots.

The arm 104 of the device 100 can be opened or deployed or pivoted outwardly from the body 102 by turning the screw 108 until the arm 104 extends to the desired extent up to its maximum travel.

Once the arm 104 is opened, then graft material can be injected through a central opening or aperture 112 defined longitudinally through the screw 108 to fill the void defined by the body 102 and open arm 104. The screw 108 provides a stop that prevents the arm 104 from being able to close unexpectedly or unintentionally.

With the arm 104 opened the device 100 provides a very stable platform that cannot tip over in the patient's vertebral disc space.

The outside profile of the device 100 includes an outward curve to the areas that contact the endplates of the adjacent vertebra to allow for a more consistent contact to the normal dishing of the end plates.

Toothed, ribbed or saw-toothed outer surfaces 114 are defined in the body 102. These surfaces reduce the likelihood of backward movement of the device 100 while still allowing for advancement through the patient's anatomy.

FIGS. 2, 3, 4, 8 and 9 show the device 100 with the arm 104 in the open, expanded or deployed configuration.

Figure 5:
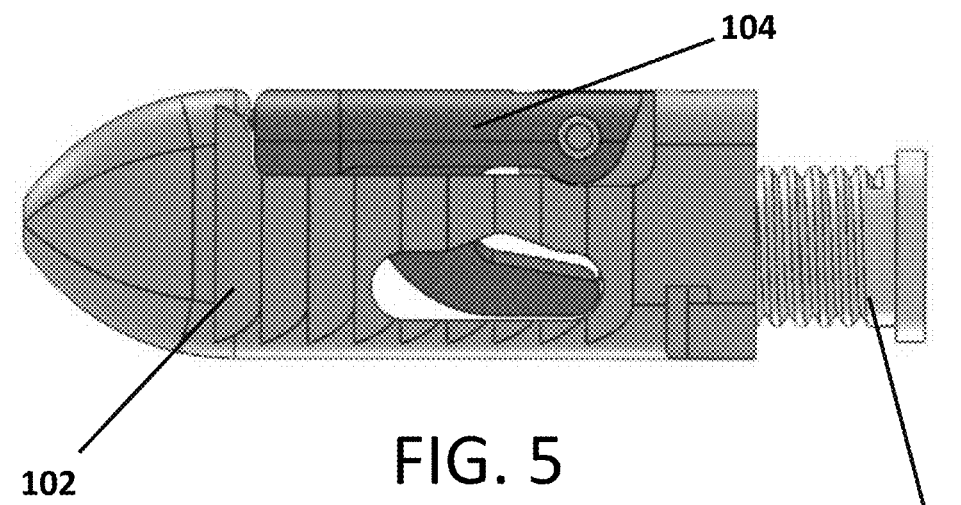
FIG. 5 depicts a side view of an embodiment of the present invention.
Figure 6:
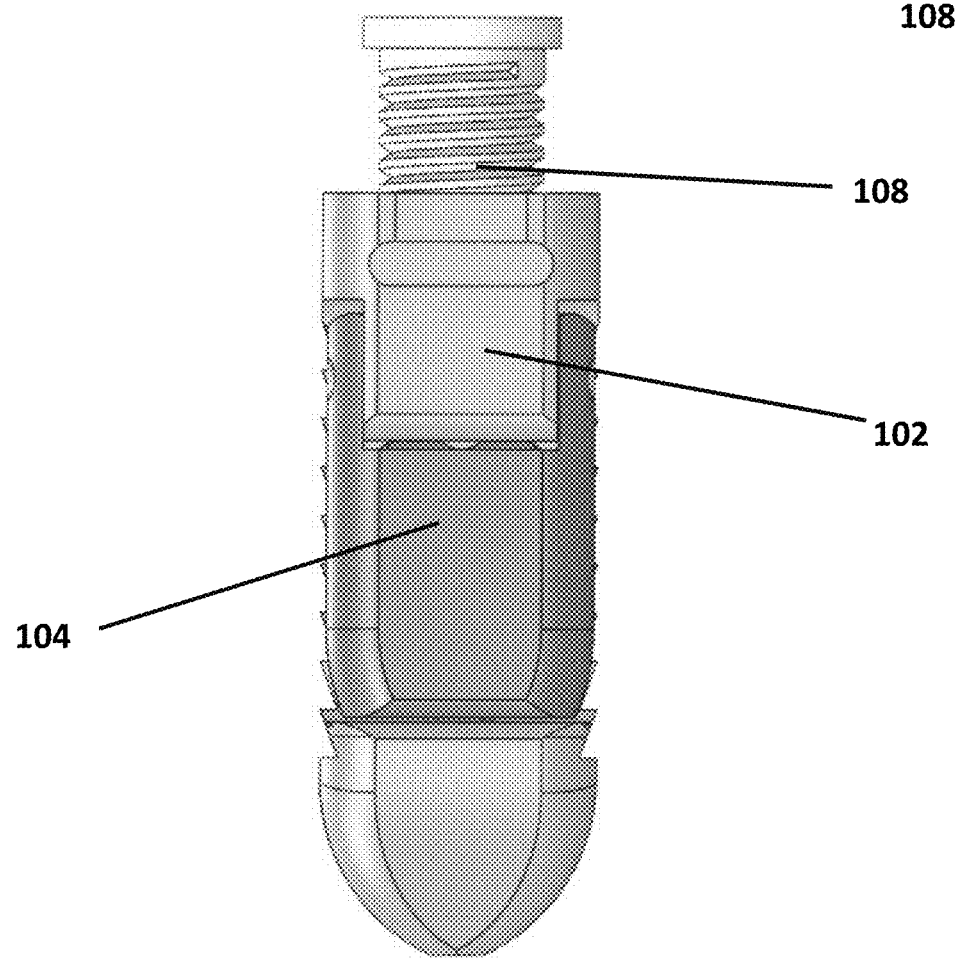
FIG. 6 depicts a top view of an embodiment of the present invention.
Figure 7:
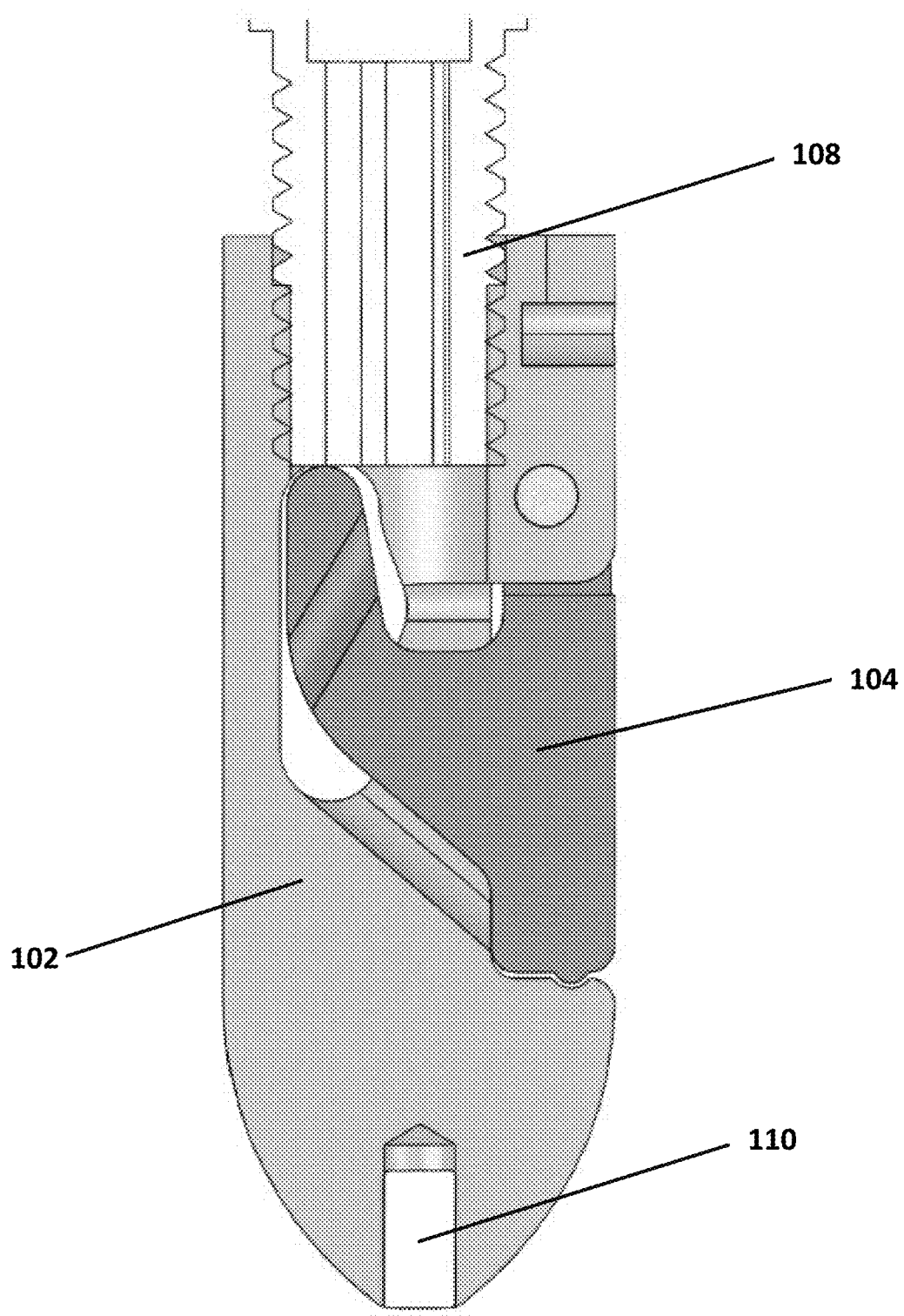
FIG. 7 depicts a side cross-sectional view of an embodiment of the present invention.

FIGS. 5, 6 and 7 show the device 100 with the arm 104 in the closed, shut, compacted or retracted configuration.

Figure 8:
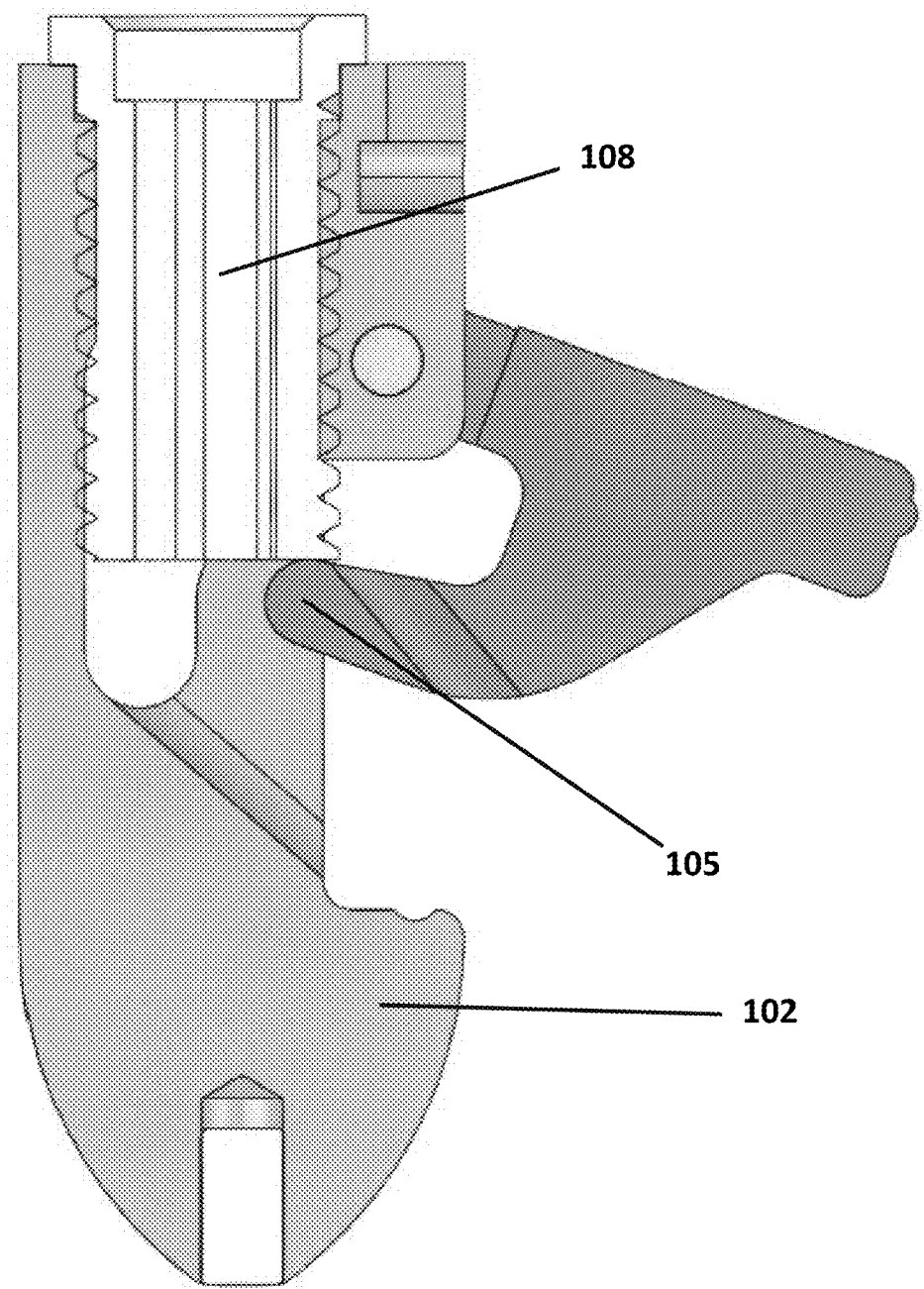
FIG. 8 depicts a side cross-sectional view of an embodiment of the present invention.
Figure 9:
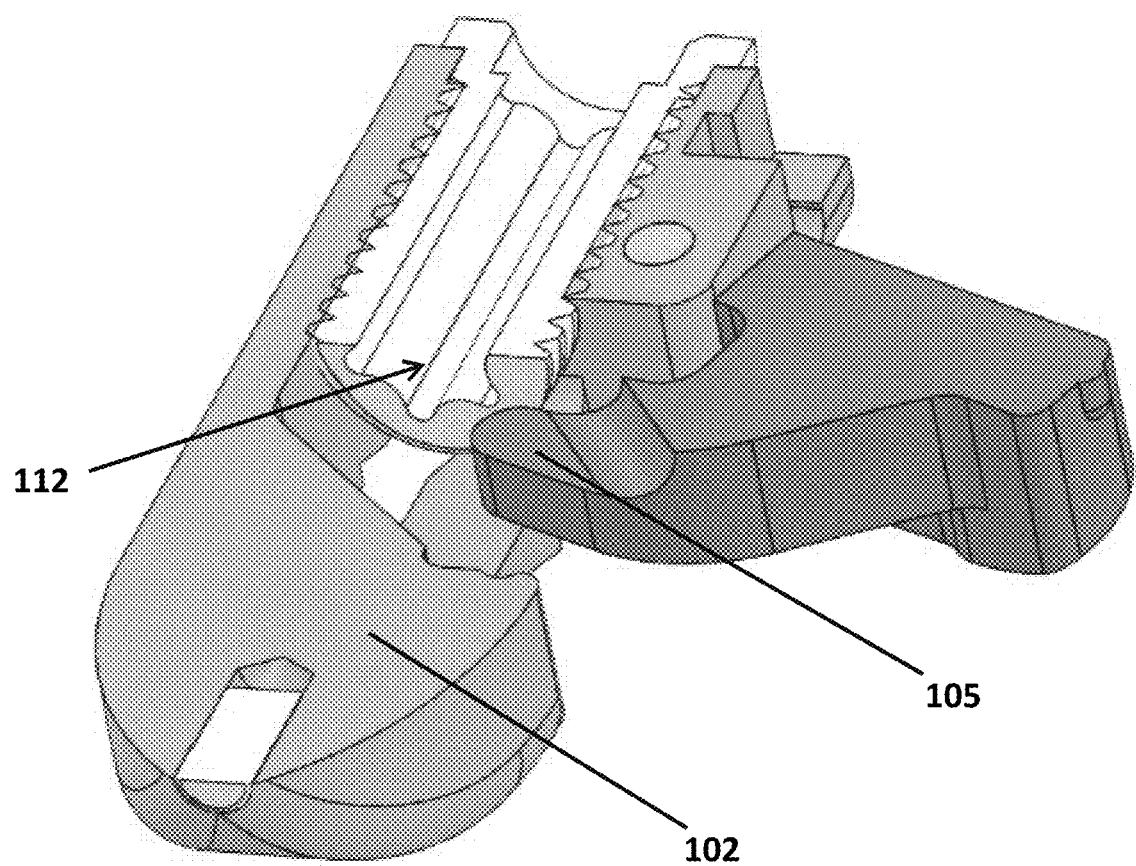
FIG. 9 depicts a perspective cross-sectional view of an embodiment of the present invention.

FIGS. 7, 8 and 9 show longitudinal cross sectional views of the device 100 so that it can be seen better how rotation of the screw 108 engages a flanged portion 105 of the arm 104 to cause the arm 104 to pivot outward from the body 102. The hollow channel 112 through the screw 108 can be clearly seen in these views.

Figure 10:
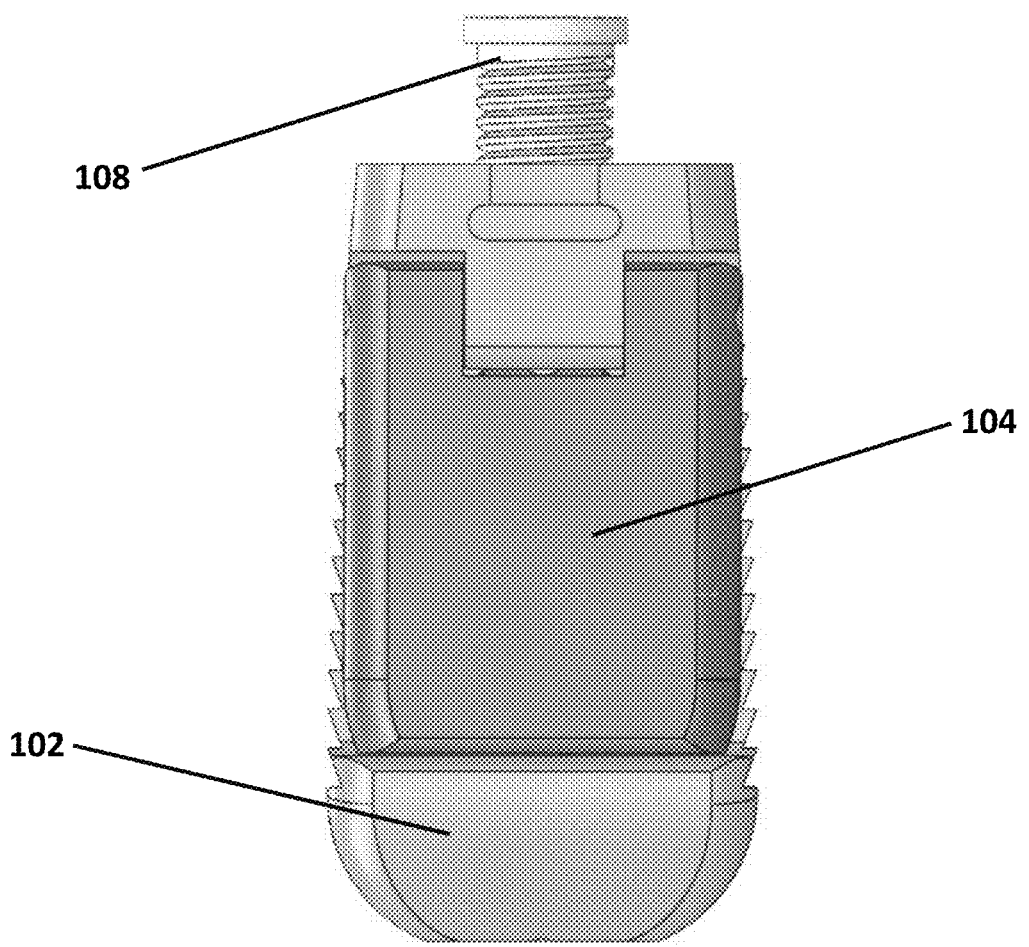
FIG. 10 depicts a top view of an embodiment of the present invention.

FIG. 10 depicts an alternative embodiment of the device 100, which has different proportions relative to the embodiment shown in FIGS. 1-9. Here, the device 100 is significantly wider relative to its length as compared to the width to length ratio of the embodiment in FIGS. 1-9. Of course, the proportions and dimensions of the device can be altered in other ways too.

A second expandable arm can be provided on an opposite side of the body. In such embodiment, the second arm side would mirror the structure of the first arm side. Thus, the single screw can still be used to actuate both arms. However, a separate screw can be provided for each arm to allow for independent adjustment of each arm.

The arm(s) can be expanded from a first closed position to a second open position, or any position therebetween, by turning the screw 104 forwardly (i.e., contracting longitudinal length of the device) or rearwardly (i.e., expanding the longitudinal length of the device).

In certain alternative embodiments, the screw-type expansion means can be replaced with alternative expansion means, such as, for example, an inflatable balloon. In further alternative embodiments, the arm may be expanded by the introduction of fill material, such as for example bone graft, bone substitute or any biocompatible fill material or any combination thereof. Expandable members or arms may be partially opened, fully opened or any opened to any position therebetween.

Although the description of the invention generally contemplates placing the device 100 of the present invention in the intervertebral space of a patient, the device 100 may also be placed within a vertebral body.

Although the description of the invention generally contemplates the body 102, arm 104, hinge pin 106 and screw 108 components comprising PEEK material, any biocompatible material or combination thereof may be used in the composition of the device 100 or its various components.

U.S. patent application Ser. No. 13/557,993, filed Jul. 25, 2012, entitled FAR LATERAL SPACER (U.S. Pub. App. No. US 2013/0079882 A1) is hereby incorporated by reference in its entirety as part of this application.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. An expandable interbody device, comprising:
a body defining a front end, a rear end and a plurality of sidewalls spanning between the front and rear ends, and a channel defined longitudinally from the rear end into the body towards the front end;
an expandable member pivotally attached to the body such that the expandable member pivots outwardly from one of the plurality of sidewalls, the expandable member defining an actuator flange that projects into the channel of the body; and
a screw threaded into the body through the rear end thereof, wherein the screw abuts the actuator flange such that advancing the screw through the channel towards the front end while contacting the actuator flange, causing the expandable member to pivot outwardly from the body,
wherein the expandable member is pivotally attached to the body via a pivot pin disposed through the body and through the expandable member.

2. The expandable interbody device of claim 1, wherein the front end of the body comprises a curved head portion.

3. The expandable interbody device of claim 1, further comprising a marker pin disposed within the body.

4. The expandable interbody device of claim 1, wherein the at least one of the plurality of sidewalls defines a sawtooth pattern portion configured to permit advancement through a patient's tissues while resisting reverse movement through the patient's tissues.

5. The expandable interbody device of claim 1, wherein the body and the expandable member are both formed of PEEK.

6. The expandable interbody device of claim 1, wherein the screw defines a channel extending through the screw along a longitudinal length direction thereof.

7. The expandable interbody device of claim 1, wherein the body has a longitudinal length defined between the front and rear ends that is greater than its lateral width defined between opposing sidewalls of the plurality of sidewalls.

8. A method of implanting an intervertebral device in a patient's spine, the method comprising:
passing an implantable device in a contracted state through Kambin's Triangle to deliver the implantable device to an intervertebral location of the patient's spine;
turning a screw disposed in the implantable device to deploy an expandable member of the implantable device; and
introducing fill material through a channel formed through the screw to fill a cavity defined in the intervertebral location by a body of the implantable device and the expandable member.

9. The method of claim 8, further comprising performing the passing step via indirect viewing of the implantable device with fluoroscopy or x-rays.

10. The method of claim 8, further comprising piercing a film disposed around at least a portion of the implantable device that is located such that the expandable member cannot expand until the film is pierced.

11. The method of claim 8, wherein the step of turning the screw disposed in the implantable device to deploy the expandable member of the implantable device includes pivoting the expandable member about a pivot point defined through an end of the expandable member.

12. An expandable interbody device, comprising:
a body defining a front end, a rear end and a plurality of sidewalls spanning between the front and rear ends, and a channel defined longitudinally from the rear end into the body towards the front end, wherein at least one of the sidewalls defines a flat outer surface portion;
an expandable member pivotally attached to the body such that the expandable member pivots outwardly from one of the plurality of sidewalls, the expandable member defining an actuator flange that projects into the body; and
a screw threaded into the body through the rear end thereof, wherein the screw abuts the actuator flange such that advancing the screw though the channel towards the front end while contacting the actuator flange causes the expandable member to pivot outwardly from the body,
wherein the expandable member is pivotally attached to the body via a pivot pin disposed through the body and through the expandable member.

13. The expandable interbody device of claim 12, wherein the front end of the body comprises a curved head portion.

14. The expandable interbody device of claim 12, further comprising a marker pin disposed within the body.

15. The expandable interbody device of claim 12, wherein the at least one of the plurality of sidewalls defines a sawtooth pattern portion configured to permit advancement through a patient's tissues while resisting reverse movement through the patient's tissues.

16. The expandable interbody device of claim 12, wherein the expandable member define a flat outer surface portion.

17. The expandable interbody device of claim 12, wherein the screw defines a channel extending through the screw along a longitudinal length direction thereof.

18. The expandable interbody device of claim 12, wherein the body has a longitudinal length defined between the front and rear ends that is greater than its lateral width defined between opposing sidewalls of the plurality of sidewalls.

* * * * *